(12) United States Patent
Gokaraju et al.

(10) Patent No.: US 10,542,989 B2
(45) Date of Patent: Jan. 28, 2020

(54) SYNERGISTIC DIETARY SUPPLEMENT COMPOSITIONS FOR ENHANCING PHYSICAL PERFORMANCE AND ENERGY LEVELS

(71) Applicant: LAILA NUTRACEUTICALS, Vijayawada (IN)

(72) Inventors: Ganga Raju Gokaraju, Vijayawada (IN); Rama Raju Gokaraju, Vijayawada (IN); Venketa Kanaka Ranga Raju Gokaraju, Vijayawada (IN); Kiran Bhupathiraju, Vijayawada (IN); Trimurtulu Golakati, Vijayawada (IN); Krishanu Sengupta, Vijayawada (IN); Venkata Krishna Raju Alluri, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 0 days.

(21) Appl. No.: 15/897,886

(22) Filed: Feb. 15, 2018

(65) Prior Publication Data
US 2018/0168655 A1    Jun. 21, 2018

Related U.S. Application Data

(62) Division of application No. 14/759,325, filed on Jul. 6, 2015, now Pat. No. 9,907,825.

(51) Int. Cl.
| | |
|---|---|
| A61K 36/00 | (2006.01) |
| A61B 17/11 | (2006.01) |
| A61F 2/06 | (2013.01) |
| A61K 36/28 | (2006.01) |
| A61K 36/9066 | (2006.01) |
| A61K 36/38 | (2006.01) |
| A61K 36/53 | (2006.01) |
| A61K 36/54 | (2006.01) |
| A23L 33/105 | (2016.01) |

(52) U.S. Cl.
CPC ............ *A61B 17/11* (2013.01); *A23L 33/105* (2016.08); *A61F 2/064* (2013.01); *A61K 36/28* (2013.01); *A61K 36/38* (2013.01); *A61K 36/53* (2013.01); *A61K 36/54* (2013.01); *A61K 36/9066* (2013.01); *A23V 2002/00* (2013.01); *A61B 2017/1107* (2013.01); *A61B 2017/1132* (2013.01); *A61B 2017/1135* (2013.01)

(58) Field of Classification Search
None
See application file for complete search history.

(56) References Cited

U.S. PATENT DOCUMENTS

| 8,017,147 | B2 | 9/2011 | Mazed | |
|---|---|---|---|---|
| 2004/0156920 | A1 | 8/2004 | Kane | |
| 2013/0189380 | A1* | 7/2013 | Gokaraju | ............. A61K 31/365 424/745 |

FOREIGN PATENT DOCUMENTS

WO    2005076750 A2    8/2005

OTHER PUBLICATIONS

Gambhire et al, Anti-inflammatory activity of aqueous extract of Cinnamomum tamala leaves by in vivo and in vitro methods. Journal of Pharmacy Research (2009), vol. 2, No. 9, pp. 1521-1524 (Year: 2009).*
Chen, Anti-inflammatory activity of mangostins from Garcinia mangostana. Food and chemical toxicology: an international journal published for the British Industrial Biological Research Association, (Feb. 2008) vol. 46, (Year: 2008).*
Begum et al, Screening of anti-inflammatory activity of Coleus aromaticus. International Journal of Chemical Sciences (2009), vol. 7, No. 4, pp. 2384-2388 (Year: 2009).*
"International Search Report for PCT/IN2014/000004 dated Jan. 21, 2015".
"The Plant List. Trachyspermum ammi", Mar. 23, 2012. Retrieved from the internet [http://www.theplantlist.org/tpl1./record/kew-2438394] viewed Jul. 6, 2015].
Chatterjee, et al., "Estimation of phenolic components and in vitro antioxidant activity of fennel (*Foenicolum vulgare*) and ajwain (*Trachyspermum ammi*) seeds", Advances in Bio Research (2012) vol. 3 (pp. 109-118).
Chidambara, "Antioxidant and antimicrobial activity of *Cissus quadrangularis* L. journal of Medicinal Food", (2003 Summer) vol. 6, No. 2, pp. 99-105.
Pyrzanowska, et al., "The influence of long-term administration of Curcuma longa extract on antioxidant processes as well as on motor activity in aged rats", Pharmacological Reports (2010) vol. 62, Suppl. 1, pp. 92-93.

\* cited by examiner

*Primary Examiner* — Qiuwen Mi
(74) *Attorney, Agent, or Firm* — Kramer Amado, P.C.

(57) ABSTRACT

The present invention discloses novel synergistic dietary supplement compositions comprising at least two ingredients selected from the extracts and fractions derived from *Sphaeranthus indicus, Coleus aromaticus, Cissus quadrangularis, Curcuma longa, Garcinia mangostana, Citrullus lanatus, Ocimum sanctum, Trachyspermum ammi* and *Cinnamomum tamala* as natural energy enhancer for enhancing physical performance, muscle strength, muscle mass, mental alertness and energy levels in a mammal.

19 Claims, No Drawings

SYNERGISTIC DIETARY SUPPLEMENT COMPOSITIONS FOR ENHANCING PHYSICAL PERFORMANCE AND ENERGY LEVELS

CROSS-REFERENCE TO RELATED APPLICATIONS

This application is a divisional of parent U.S. application Ser. No. 14/759,325, filed on Jul. 6, 2015; which is a national stage application based on International Application No. PCT/IN2014/000004, filed on Jan. 2, 2014, and published as International Publication No. WO 2014/106860; which claims priority to Indian Application No. 27/CHE/2013, filed on Jan. 3, 2013. The disclosure of each prior application is incorporated by reference herein in its entirety.

TECHNICAL FIELD OF THE INVENTION

The present invention relates to novel synergistic dietary supplement compositions comprising at least two ingredients selected from the extracts and fractions derived from *Sphaeranthus indicus, Coleus aromaticus, Cissus quadrangularis, Curcuma longa, Garcinia mangostana, Citrullus lanatus, Ocimum sanctum* and *Cinnamomum tamala* as natural energy enhancer for enhancing physical performance, muscle strength and energy levels in a mammal.

The present invention further relates to food ingredient formulations such as beverages, dietary ingredient formulation, snacks and energy drinks containing the said herbal ingredient or its compositions for onset and steady maintenance of energy, muscle strength and mental alertness and for enhancing muscle power, physical activity, physical fitness, mental alertness, energy levels, stamina levels, circulatory health, blood vessel health or for better physical and mental health.

BACKGROUND OF THE INVENTION

The basic force and condition behind all activities of human life is the presence of energy. Energy is the vital principle needed to sustain life and it is required for every aspect of existence—every act uses energy—thinking, feeling, walking, eating, drinking, dreaming, breathing etc. Energy is felt and experienced upon its expenditure. The energy we experience immediately after eating (such as sweets), or the hype we get following the consumption of coffee is from the expenditure of energy from body's energy reserves, not through its accumulation. Age, fatigue and stress make people feel deficient in energy. This drag in energy very often compromises body's mental alertness. The efficiency at work place and in personal management can be enhanced by addressing body's energy demands properly.

Dietary supplements are used by physically active people or weak people to increase their physical performance, physical fitness, improve their health, or reduce the potentially negative consequences of physical activity such as injury and chronic fatigue, or suppressed immune function.

Many energy beverages, supplements and food ingredient formulations are presently available in the market, but they are fully loaded with disaccharides, carbohydrate complexes, proteins, amino acids and vitamins along with numerous other agents. Many of these formulations act too quickly to give instant energy and not sustain the levels over period of time. Besides, these formulations tend to increase the blood glucose levels sharply and this is followed by their rapid depletion. This might sometimes lead to complications. Natural supplements, which improve the feeling of being energetic, general agility, endurance and mental alertness are thus in great demand. Many research groups across the globe are working on developing a superior product to address the above requirements.

Therefore, the present invention addresses the existing need in the art by providing an extracts, fractions or compositions that provides energy and/or mental alertness. Thus, the present invention provides ingredient(s) and/or composition(s) capable of increasing energy levels for an extended period of time in a mammal to enhance energy levels, muscle power and mental alertness and thus solves these needs.

SUMMARY OF THE INVENTION

The present invention provides novel synergistic dietary supplement compositions comprising at least two ingredients/components selected from the extracts or fractions derived from *Sphaeranthus indicus, Coleus aromaticus, Cissus quadrangularis, Curcuma longa, Garcinia mangostana, Citrullus lanatus, Ocimum sanctum* and *Cinnamomum tamala*, which are capable of increasing energy levels for an extended period of time, improve muscle power and mental alertness.

In an important aspect, the invention provides novel synergistic dietary supplement compositions comprising at least two ingredients/components selected from the extracts or fractions derived from *Sphaeranthus indicus, Coleus aromaticus, Cissus quadrangularis, Curcuma longa, Garcinia mangostana, Citrullus lanatus, Ocimum sanctum* and *Cinnamomum tamala* for the onset and steady maintenance of energy, muscle strength and mental alertness and for enhancing muscle power, muscle mass, physical activity, physical fitness, mental alertness, energy levels, stamina levels, circulatory health, blood vessel health or for better physical and mental health in a mammal.

In another aspect, the invention provides dietary supplements, food ingredient formulations such as beverages, snacks and energy drinks containing the above said ingredient(s) or its composition(s) for the onset and steady maintenance of energy and mental alertness. The formulation is useful for enhancing muscle power, physical activity, physical fitness, mental alertness, muscle mass, energy levels, stamina levels, circulatory health, blood vessel health or for better physical and mental health in a mammal.

In yet another aspect, the invention provides novel synergistic dietary supplement compositions comprising at least two ingredients selected from the extracts and fractions derived from *Sphaeranthus indicus, Coleus aromaticus, Cissus quadrangularis, Curcuma longa, Garcinia mangostana, Citrullus lanatus, Ocimum sanctum* and *Cinnamomum tamala* and optionally in combination with at least one ingredient selected from active compound(s), phytochemical(s), derived from plant(s), animal(s) or microorganisms with proven therapeutic health benefits; pharmaceutically or dietetically acceptable agents, active ingredients, vitamins, amino acids and minerals.

In yet another aspect, the invention comprising compositions derived from *Sphaeranthus indicus, Coleus aromaticus, Cissus quadrangularis, Curcuma longa, Garcinia mangostana, Citrullus lanatus, Ocimum sanctum* and *Cinnamomum tamala* for onset and steady maintenance of energy; muscle strength, mental alertness and for enhancing muscle power, muscle mass, physical activity, physical fitness, mental alertness, energy levels, stamina levels, circulatory health, blood vessel health or for better mental health in warm blooded animals in need thereof.

In yet another aspect, the invention provides a method of increasing energy to provide an onset and steady maintenance of energy, muscle strength and mental alertness in a mammal, wherein the method comprises supplementing or treating the said mammal with the compositions comprising at least two ingredients selected from the extracts and fractions, derived from *Sphaeranthus indicus, Coleus aromaticus, Cissus quadrangularis, Curcuma longa, Garcinia mangostana, Citrullus lanatus, Ocimum sanctum* and *Cinnamomum tamala*.

DETAILED DESCRIPTION OF THE INVENTION

The invention will now be described in detail in connection with certain preferred and optional embodiments, so that various aspects thereof may be more fully understood and appreciated. However, any skilled person will appreciate the extent to which such embodiments could be extrapolated in practice.

Source of the Plant Materials:

The plants used in the present invention viz., *Sphaeranthus indicus, Coleus aromaticus, Cissus quadrangularis, Curcuma longa, Cinnamomum tamala, Citrullus lanatus* and *Ocimum sanctum* were collected from the plants originated in India and *Garcinia mangostana* was of South East Asian origin, mostly from Indonesia. It is presently being cultivated in South India.

Rationale of Performing NO Assay, ATP Assay and Protein Assay

The basic force and condition behind all activities of human life is the presence of energy. It is thus essential that during exercise we require more nutrients and oxygen through enhanced blood circulation in working muscles. Nitric oxide produced by vascular endothelial cells is known as a potent vasodilator, which makes blood vessels to expand thus providing more supply of oxygen and nutrients to the muscle cells during workouts. Thus it helps in prolonging the endurance during exercise and physical activities.

Adenosine Triphosphate or ATP supplies the chemical energy that fuels muscular activities. For the first 5 or 6 seconds of muscle power, muscular activity is dependent on the pool of ATP that is already present in the muscle cells. Beyond this time, new amounts of ATP must be formed to enable the activation of muscular contractions that are needed to support longer and more vigorous physical activities. Therefore, it is essential to increase the intracellular energy source or ATP content during endurance exercise or for longer and intense period of physical activities.

Protein is an important component of every cell in the body. Proteins are synthesized in the cells through translation process of mRNA utilizing amino acids. It is the primary building block of muscles, bones and cartilage; and is essential for muscle growth and repair. Therefore, stimulation of muscle protein synthesis is a very important and crucial factor for increasing muscle mass.

Based on the above, we hypothesized that the herbal extracts, fractions or their compositions/formulations which can enhance nitric oxide synthesis in endothelial cells; increase ATP content and trigger protein synthesis in skeletal muscle cells would be ideally promising for increasing energy and endurance level, and muscle mass in physical performers such as body builders, athletes etc. Therefore, we intended to screen the herbal extracts and their compositions to assess their ability to increase the synthesis of nitric oxide in endothelial cells, intracellular ATP and protein in skeletal muscle cells.

In the present invention, a large number of extracts derived from plant materials were screened using cell based assays for the modulation of nitric oxide, ATP and protein synthesis. During the study it was found surprisingly that the extracts or fractions derived from *Sphaeranthus indicus, Coleus aromaticus, Cissus quadrangularis, Curcuma longa, Garcinia mangostana, Cinnamomum tamala, Citrullus lanatus* and *Ocimum sanctum* potently modulates nitric oxide (Table 1), ATP (Table 6) and protein synthesis (Table 7). To further obtain a product with improved activity, the extracts or fractions of above plants were combined at different ratios and the compositions so obtained were tested for the modulation of nitric oxide, ATP and protein synthesis. It was found surprisingly that the compositions comprising at least two extracts derived from *Sphaeranthus indicus, Coleus aromaticus, Cissus quadrangularis, Curcuma longa, Garcinia mangostana* or *Cinnamomum tamala* shows synergistic enhancement of nitric oxide, ATP and protein synthesis. *Sphaeranthus indicus* extract (LI12500) and its composition (LI12522F2) in combination with *Coleus aromaticus* extract (LI34103); *Cissus quadrangularis* extract (LI05704), and its composition (LI89032F3) in combination with *Curcuma longa* extract (LI09703) and *Garcinia mangostana* extract (LI80013) and its composition (LI80020F3) in combination with *Cinnamomum tamala* extract (LI33603) were assessed for their efficacy as energy booster and muscle building dietary supplements in a protein assay using L6 rat skeletal muscle cells, as nitric oxide enhancer using nitrate assay in ECV304 human endothelial cells and as ATP enhancer using ATP assay in L6 rat skeletal muscle cells. The compositions LI12522F2, LI89032F3 and LI80020F3 were found surprisingly to be synergistic as they exhibited better efficacy when compared to their respective individual ingredients.

The efficacy of the compositions LI12522F2, LI89032F3 and LI80020F3 for enhancing energy and endurance was further evaluated in an animal study. Swiss albino mice were orally treated with vehicle or 150 mg/kg of LI89032F3 or LI12522F2 or LI80020F3 or 150 mg/kg of L-Carnitine or 10 mg/kg Caffeine for 21 days. On day 21, one hour after the treatment the mice were forced to swim with a constant load (10% of its body weight attached to its tail) in an acrylic cylinder filled with water. This test was monitored for 10 minutes using the SMART video tracking system (Panlab S.L.U). Various swimming parameters were recorded and analyzed by smart software. The animals treated with the compositions showed reduced resting time and enhanced slow moving time, fast moving time, total moving time, path length of swimming and average velocity compared to the controlled treated animals as summarized in table 8.

Similarly, after 21 days of treatment, the grip strength of mice was measured by using Grip strength meter (UgoBasile, Italy). Animals were trained and habituated to the experimental environment and conditions for 5 days. Each mice was allowed to grasp the grasping bar and it was pulled back gently in a horizontal plane by tail with gradually increasing force till the pulling force overcomes the grip strength of the animal. The force applied at the moment when the mice leaves its grasp on the grasping bar was recorded as grip strength in grams. The animals supplemented with the compositions LI89032F3 or LI12522F2 or LI80020F3 showed improved grip strength compared to the animals treated with control or positive controls (L-Carnitine or Caffeine) as summarized in Table 9.

Hence, it is evident that supplementation of extracts or fractions derived from *Sphaeranthus indicus, Coleus aromaticus, Cissus quadrangularis, Curcuma longa, Garcinia mangostana* and *Cinnamomum tamala* and their compositions (LI12522F2, LI89032F3 and LI80020F3) can increase the energy levels and endurance potential.

The forgoing demonstrates that *Sphaeranthus indicus* extract and its composition in combination with *Coleus aromaticus* extract (LI12522F2); *Cissus quadrangularis* extract, and its composition in combination with *Curcuma longa* extract (LI89032F3) and *Garcinia mangostana* extract and its composition in combination with *Cinnamomum tamala* extract (LI80020F3) could be potent natural supplements to provide an onset, steady maintenance of energy, muscle strength, physical endurance and mental alertness in humans and animals.

Accordingly, in a preferred embodiment the present invention discloses novel synergistic compositions comprising at least two extracts or fractions derived from *Sphaeranthus indicus, Coleus aromaticus, Cissus quadrangularis, Curcuma longa, Garcinia mangostana, Citrullus lanatus, Oscimum sanctum* and *Cinnamomum tamala*, capable of increasing energy levels for an extended period of time and mental alertness and to increase muscle strength.

In another embodiment the invention discloses compositions comprising at least two ingredients selected herbal extracts or fractions derived from *Sphaeranthus indicus, Coleus aromaticus, Cissus quadrangularis, Curcuma longa, Garcinia mangostana, Citrullus lanatus, Ocimum sanctum* and *Cinnamomum tamala* for the onset and steady maintenance of energy, muscle strength and mental alertness, wherein, the herbal extracts or fractions and their compositions are useful for enhancing muscle strength, physical activity, physical fitness, mental alertness, energy levels, stamina levels, circulatory health, blood vessel health or for better physical and mental health in a mammal.

In another embodiment, the invention discloses herbal extracts or fractions derived from *Sphaeranthus indicus, Coleus aromaticus, Cissus quadrangularis, Curcuma longa, Garcinia mangostana, Citrulus lanatus, Oscimun sanctum* and *Cinnamomum tamala* and their compositions, which contain optionally at least one biologically active ingredient selected from extract of *Ocimum basilicum, Zingiber officinalis, Tribulus terrestris, Trachyspermum ammi, Mentha arvensis, Piper cubeba, Foeniculum vulgare*, vitamins, amino acids, taurine, an extract of *Ginkgo biloba, Rhodiola* and an extract of guarana, melatonin green tea as a natural energy enhancer to provide an onset and steady maintenance of energy, muscle strength and mental alertness in a warm blooded animal or mammal in need thereof.

In yet another embodiment, the invention discloses compositions comprising at least two ingredients selected from herbal extracts or fractions derived from *Sphaeranthus indicus, Coleus aromaticus, Cissus quadrangularis, Curcuma longa, Garcinia mangostana, Citrullus lanatus, Ocimum sanctum* and *Cinnamomum tamala*, which further contain optionally at least one ingredient selected from excipient, diluent, sweeteners, flavorants colorants, vitamins or amino acids, as a natural energy enhancer for enhancing physical or mental performance, onset and steady maintenance of energy enhancing physical activity, physical fitness, mental alertness, energy levels, stamina levels, circulatory health, blood vessel health or for better mental health in a mammal.

In another embodiment, examples of improved physical performance include increased stamina and improved speed, strength, power, endurance, flexibility, agility, balance, focus coordination, reaction time, fatigue recovery and also increase of sex stamina. Examples of improved mental performance include improved sharpness, attention span, mental alertness, cognitive functions, mood elevation, and recovery or reduction of mental fatigue (e.g., following a high-intensity physical exercise).

In another embodiment, the invention includes dietary supplements, food ingredient formulations such as beverages, snacks and energy drinks containing the above said ingredient(s) or its composition(s) for enhancing, muscle strength, physical activity, physical fitness, mental alertness, energy levels, stamina levels, circulatory health, blood vessel health or for better mental health in warm blooded animals in need thereof.

In another embodiment, the invention provides a method of increasing natural energy to provide an onset and steady maintenance of energy and mental alertness in a mammal, wherein the method comprises supplementing or treating the said mammal with a composition comprising at least two ingredients selected from extracts or fractions derived from *Sphaeranthus indicus, Coleus aromaticus, Cissus quadrangularis, Curcuma longa, Garcinia mangostana, Citrullus lanatus, Ocimum sanctum* and *Cinnamomum tamala*.

In yet another embodiment, the invention provides compositions comprising at least two ingredients selected from the herbal extracts or fractions derived from *Sphaeranthus indicus, Coleus aromaticus, Cissus quadrangularis, Curcuma longa, Garcinia mangostana* and *Cinnamomum tamala* as natural enhancers of energy instantly, muscle power and physical performance in warm blooded animals in need thereof.

In yet another embodiment the invention provides compositions comprising said biologically active ingredients as described in combination with one or more components selected from extract(s), fraction(s), active compound(s), phytochemical(s); powder(s) derived from plant(s), animal(s) or microorganisms with proven therapeutic health benefits; pharmaceutically or dietetically acceptable agents, active ingredients, vitamins, amino acids or minerals.

In a further exemplary embodiment, the composition of the present invention may further contain optionally one or more of the non-limiting components such as vitamins selected from B vitamins, including thiamine, riboflavin, niacin, pantothenic acid, pyridoxine, biotin, cyanocobalamin, choline and/or folic acid, including the reduced forms of folic acid such as but not limited to folinic acid, calcium folinate and methyltetrahydrofolate. The B-complex vitamins are also water soluble vitamins that aid the breakdown of carbohydrates into glucose to provide energy for the body, the breakdown of fats and proteins to aid the normal functioning of the nervous system, and muscle tone in the stomach and intestinal tract. Particular forms of B vitamins in the composition may include d-Calcium pantothenate, niacinamide, pyridoxine hydrochloride, and thiamine mononitrate; or amino acids.

In another embodiment, the composition comprising at least two herbal extracts or fractions derived from *Sphaeranthus indicus, Coleus aromaticus, Cissus quadrangularis, Curcuma longa, Garcinia mangostana, Citrullus lanatus, Ocimum sanctum* and *Cinnamomum tamala* increases circulation, metabolism efficiency, regulates neurotransmitters and boosts oxygen levels in the brain. Benefits of enhanced circulation in the brain include improved short and long term memory, increased reaction time and improved mental clarity.

In another embodiment the said herbal extracts or fractions or their composition(s) can be taken e.g. by performance athletes, those engaged in endurance and multidiscipline sports, aged and sick persons in order to increase mental alertness, stamina levels, muscle strength, physical fitness and to maintain the onset and steady maintenance of energy, muscle strength. The present ingredients and compositions may be formulated as a "fitness drink" that can be taken with breakfast or in the form of a concentrate from which such a drink can be regularly used.

The composition wherein, the concentration of *Sphaeranthus indicus, Coleus aromaticus, Cissus quadrangularis, Curcuma longa, Garcinia mangostana, Citrullus lanatus, Ocimum sanctum* and *Cinnamomum tamala* derived ingredients in the composition individually or jointly varies from 0.01% to 99.99%.

The composition wherein, the concentration of *Sphaeranthus indicus, Coleus aromaticus, Cissus quadrangularis, Curcuma longa, Garcinia mangostana, Citrullus lanatus, Ocimum sanctum* and *Cinnamomum tamala, Ocimum basilicum, Zingiber officinalis, Tribulus terrestris, Trachyspermum ammi, Mentha arvensis, Piper cubeba* and *Foeniculum vulgare* derived ingredients in the composition individually or jointly varies from 20% to 80%.

In another embodiment, the herbal extracts or fractions or composition(s) of the present invention are useful to improve aerobic performance and capacity by influencing lactic acid metabolism and reducing fatigue as well as for alleviation of one or more of the biological energy markers including but not limited to ATP levels/production; Nitric Oxide levels, NADH balance, leptin levels and adipocytes derived peptides.

In another embodiment, the method of ameliorating the biomarkers selected from ATP, Nitric Oxide, e.Nos, MAO, ACHE, Muscle protein, Miogenin and Enhancing muscle cell proliferation wherein the method comprises administering to a subject or mammal or warm blooded animal a therapeutically effective quantity of the composition comprising herbal extracts or fractions or compositions derived from *Sphaeranthus indicus, Coleus aromaticus, Cissus quadrangularis, Curcuma longa, Garcinia mangostana, Citrullus lanatus, Ocimum sanctum* and *Cinnamomum tamala*, which contain optionally at least one biologically active ingredient selected from the extracts or fractions from *Ocimum basilicum, Zingiber officinalis, Tribulus terrestris, Trachyspermum ammi, Mentha arvensis, Piper cubeba* and *Foeniculum vulgare*.

In another embodiment, the herbal extracts or fractions or composition(s) can further be combined with one or more biological active ingredients comprising anti-diabetic, anti-hyperlipidemic, anti-obesity, anti-hypertensive, anti-platelet aggregation, anti-infective, anti-atherosclerotic, anti-inflammatory, anti-oxidant and bio-enhancing activity.

In a further exemplary embodiment, the composition may further contain an effervescent agent comprising a dietary acceptable acid and a base to produce CO2 gas upon contact with water.

In another exemplary embodiment, the composition may be dissolved in water or in other liquids suitable for human consumption.

In another embodiment of the invention the various suitable solvents that can be used for preparing the extracts and fractions or extracting or fractionating the herbs *Sphaeranthus indicus, Coleus aromaticus, Cissus quadrangularis, Curcuma longa, Garcinia mangostana* and *Cinnamomum tamala* include but not limited to C1-C5 alcohols, like ethanol, methanol; water and mixtures thereof; C1-C7 hydrocarbons such as hexane; esters like ethyl acetate and the like and mixtures thereof.

In another embodiment of the invention, the plant parts for preparing the extracts can be selected from leaves, stems, fruit, fruit ring, flower heads, root, bark or whole plant or mixtures thereof.

In another embodiment, the extracts or fractions or composition(s) of the present invention may be formulated in dry form, liquid form, food product, dietary supplement or any suitable form such as tablet, a capsule or a soft chew.

In another embodiment the extracts or fractions or composition(s) can be delivered in the form of controlled release tablets, using controlled release polymer-based coatings by the techniques including nanotechnology, microencapsulation, colloidal carrier systems and other drug delivery systems.

In another embodiment of the invention provides the extracts or fractions or composition(s) nutritional/dietary supplements can be contemplated/made in the dosage form of healthy foods, or food for specified health uses such as solid food like chocolate or nutritional bars, semisolid food like cream or jam, or gel and also beverage and the like, such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

The flavorant(s) that may be included in the composition are not relevant to the inventive concepts disclosed herein, and those skilled in the art are familiar with the wide range of flavorants available. Therefore, any suitable flavorant or combination of flavorants, natural and/or artificial, is within the contemplated scope of the present disclosure.

In another exemplary embodiment, the composition may further include food colorants to improve the visual appearance of a drink prepared with the composition.

In other embodiment, the extracts or fractions or composition(s) of this invention are useful in treating mitochondrial deficiencies in both humans and animals. It also can be used for enhancing or maintaining physical or mental performance, reducing infection in physically stressed athletes or non-athletes from intense physical exercises. Moreover, it can be an activator of Sirtuin.

In another exemplary embodiment the biologically acceptable ingredients or compositions can further be combined with one or more pharmaceutically or dietetically acceptable excipients, carriers and diluents, comprising glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, preservatives, distilled water, saline, aqueous glucose solution, alcohol, propylene glycol and polyethylene glycol, various animal and vegetable oils, white soft paraffin, paraffin and wax.

In still another embodiment, the invention features a method of enhancing physical or mental performance, steady maintenance of energy, physical endurance, muscle mass, muscle strength and mental alertness in humans and animals, wherein the method comprises administering to a subject in need thereof an effective amount of a compositions comprising at least two ingredients selected from the herbal extracts or fractions derived from *Sphaeranthus indicus, Coleus aromaticus, Cissus quadrangularis, Curcuma longa, Garcinia mangostana, Citrullus lanatus, Ocimum* sanctum and *Cinnamomum tamala*. Examples of improved physical performance include increased stamina and improved speed, strength, power, endurance, flexibility, agility, balance, focus coordination, reaction time, fatigue recovery and also increase of sex stamina. Examples of improved mental performance include improved sharpness, attention span, mental alertness, cognitive functions, mood elevation, and recovery or reduction of mental fatigue (e.g., following a high-intensity physical exercise).

In still another embodiment of the invention, the compositions comprising at least two ingredients selected from the extracts and fractions derived from *Sphaeranthus indicus, Coleus aromaticus, Cissus quadrangularis, Curcuma longa, Garcinia mangostana* and *Cinnamomum tamala* can be used for the preparation of a medicament useful for enhancing physical or mental performance, steady maintenance of energy, muscle strength, physical endurance and mental alertness in humans and animals.

Those of ordinary skill in the art will appreciate that changes could be made to the embodiments described above without departing from the broad inventive concept thereof. It is understood, therefore, that this invention is not limited to the particular embodiments or examples disclosed, but is intended to cover modifications within the objectives and scope of the present invention as defined in the specification. The presented examples illustrate the invention, but they should not be considered to limit the scope of the invention in any way.

EXAMPLES

Example 1: Preparation of *Garcinia mangostana* Methanol Extracts (L180013)

*Garcinia mangostana* fruit rind (1 kg) were pulverized and the powder taken in a RB flask and extracted with methanol (10 L) at 80° C. temperature for 2 h. The extract was filtered and the spent raw material was re-extracted twice with methanol (2×6 L) under similar conditions. The combined extract was fine filtered and concentrated over a climbing film evaporator to obtain a residue (LI80013).

The methanol extracts of *Coleus aromaticus* Leave(s), Root(s) of *Curcuma longa*, Flower heads) of *Sphaeranthus indicus*, Leave(s) of *Cinnamomum tamala*, Fruit rind of *Citrullus lanatus* and Whole plant of *Ocimum sanctum* were prepared using the similar procedure.

Example 2: *Sphaeranthus indicus* Ethyl Acetate Extract (L112500)

*Sphaeranthus indicus* flower heads (2.2 kg) were charged into a pilot extractor and extracted with ethyl acetate (22 L) at reflux temperature for 2 h. The extract was filtered and the spent raw material was re-extracted twice with ethyl acetate (2×13 L) under similar conditions. The combined extract was fine filtered and concentrated over a climbing film evaporator to obtain residue (174 g).

The ethyl acetate extracts of *Coleus aromaticus* Leave(s), Root(s) of *Curcuma longa*, Fruit rind of *Garcinia mangostana*, Leave(s) of *Cinnamomum tamala*, Fruit rind of *Citrullus lanatus* and Whole plant of *Ocimum sanctum* were prepared using the similar procedure.

Example 3: Preparation of *Cissus quadrangularis* (LI05704) Ethanol Extract

*Cissus quadrangularis* stems (1 kg) were pulverized and the powder taken in a RB flask and extracted with ethanol (8 L) at 80° C. temperature for 2 h. The extract was filtered and the spent raw material was re-extracted twice with ethanol (2×6 L) under similar conditions. The combined extract was fine filtered and concentrated over a climbing film evaporator to obtain as residue L105704 as a residue (96 g).

The plant materials of other herbs Flower heads of *Sphaeranthus indicus*, Leave(s) of *Coleus aromaticus*, Root(s) of *Curcuma longa*, Fruit Rind of *Garcinia mangostana*, Leave(s) of *Cinnamomum tamala*, Fruit Rind of *Citrullus lanatus* and Whole plant of *Ocimum sanctum* were subjected to similar extraction procedure to obtain their ethanol extracts. Water and hydro-alcohol extracts were also prepared using similar procedure.

Example 4: Compositions

Composition-1 (LI12522F2): The composition-1 (LI12522F2) was prepared by combining the methanol extract of *Sphaeranthus indicus* (LI12500) and methanol extract of *Coleus aromaticus* (LI34103), in the ratio of 2:1.

Composition-2 (LI89032F3): The composition-2 (LI89032F3) was prepared by combining the ethanol extract of *Cissus quadrangularis* (LI05704) and methanol extract of *Curcuma longa* (LI09703), in the ratio of 1:2.

Composition-3 (LI80020F3): The composition-3 (LI80020F3) was prepared by combining the methanol extract of *Garcinia mangostana* (LI80013) and methanol extract of *Cinnamomum tamala* (LI33603), in the ratio of 1:2.

Composition-4 (LI12532F1): The composition-4 (LI12532F1) was prepared by combining the methanol extract of *Sphaeranthus indicus* (LI12500), ethanol extract of *Coleus aromaticus* (LI34103) and methanol extract of *Garcinia mangostana* (LI80013), in the ratio of 3:1:1.

Composition-5 (LI12532F3): The composition-5 (LI12532F3) was prepared by combining the methanol extract of *Sphaeranthus indicus* (LI12500), ethanol extract of *Coleus aromaticus* (LI34103) and methanol extract of *Garcinia mangostana* (LI80013), in the ratio of 2:1:2.

Composition-6 (LI12532F4): The composition-6 (LI12532F4) was prepared by combining the methanol extract of *Sphaeranthus indicus* (LI12500), ethanol extract of *Coleus aromaticus* (LI34103) and methanol extract of *Garcinia mangostana* (LI80013), in the ratio of 1:8:1.

Composition-7 (LI89034F1): The composition-7 (LI89034F1) was prepared by combining the ethanol extract of *Cissus quadrangularis* (LI05704), methanol extract of *Curcuma longa* (LI09703) and ethanol extract *Trachyspermum ammi* (LI12304), in the ratio of 1:2:1.

Composition-8 (LI89034F2): The composition-8 (LI89034F3) was prepared by combining the ethanol extract of *Cissus quadrangularis* (LI05704), methanol extract of *Curcuma longa* (LI09703) and ethanol extract *Trachyspermum ammi* (LI12304), in the ratio of 2:1:2.

Composition-9 (LI89034F4): The composition-9 (LI89034F4) was prepared by combining the ethanol extract of *Cissus quadrangularis* (LI05704), methanol extract of *Curcuma longa* (LI09703) and ethanol extract *Trachyspermum ammi* (LI12304), in the ratio of 1:8:1.

Composition 10: The composition-10 was prepared by combining the methanol extract of *Sphaeranthus indicus* (LI12500), ethanol extract of *Trachyspermum ammi* (LI12304) and methanol extract of *Garcinia mangostana* (LI80013), in the ratio of 1:8:1.

Composition 11: The composition-10 was prepared by combining the methanol extract of *Sphaeranthus indicus* (LI12500), ethanol extract of *Cissus quadrangularis*

(LI05704) and methanol extract of *Garcinia mangostana* (LI80013), in the ratio of 1:8:1.

Example 5: Nitrite Assay

A study was conducted using *Sphaeranthus indicus* extract (LI12500) and its compositions (LI12522F2 and LI12532F1); *Cissus quadrangularis* extract (LI05704), and its compositions (LI89032F3 and LI89034F1; *Garcinia mangostana* extract (LI80013) and its composition (LI80020F3) in combination with *Cinnamomum tamala* extract (LI33603); *Citrullus lanatus* extract (LI/PD/151/01R1) and *Ocimum sanctum* extract (LI/PD/014/03R1) to evaluate whether these individual extracts and compositions can induce nitric oxide generation in human endothelial cells. The nitrite concentration in human endothelial culture supernatants from the cells treated with the test substances was measured in comparison with the control treated cell culture supernatants. Briefly, equal number of ECV304 human endothelial cells ($1.5 \times 10^5$) was plated in 35 mm culture dish. After attachment of the cells, the culture dishes were washed twice with Hank's Buffered Salt Solution (HESS) and the cells were treated with different concentrations of extracts and compositions in 1 ml □-MEM supplemented with 1% FBS for 4 h. The vehicle control cultures received 0.2% DMSO. The cell free culture supernatants were collected and nitrite content was estimated using Griess assay. Fifty micro liters of culture supernatants were mixed with equal volume of Griess reagent (a mixture containing 1:1 ratio of 0.2% naphthylenediaminedihydrochloride and 2% sulphanilamide in 5% phosphoric acid) in each well of a micro-titer plate and incubated further for 10 min in room temperature. The color development was measured at 550 nm in a microplate reader Spectra MaxM5 (Molecular devices, Sunnyvale, Calif.). Standard curves were constructed with known concentrations of sodium nitrite and the data is summarized in table 1.

TABLE 1

| S. No. | Test Product at the Dose of 10 µg/ml | Code | Nitrite Concentration (%) |
|---|---|---|---|
| 1. | *S. indicus* extract | LI12500 | 10.64 |
| 2. | *C. aromaticus* extract | LI34103 | −1.80 |
| 3. | Composition-1 | LI12522F2 | 20.80 |
| 4. | *C. quadrangularis* extract | LI05704 | 47.90 |
| 5. | *C. longa* extract | LI09703 | 269.07 |
| 6. | Composition-2 | LI89032F3 | 359.08 |
| 7. | *G. mangostana* extract | LI80013 | 50.87 |
| 8. | *C. tamala* extract | LI33603 | 16.66 |
| 9. | Composition-3 | LI80020F3 | 58.26 |
| 10. | *C. lanatus* extract | LI/PD/151/01R1 | 33.03 |
| 11. | *O. sanctum* extract | LI/PD/014/03R1 | 18.53 |

The above nitrite concentration values (Table 1), clearly shows the synergistic efficacy of the compositions in enhancing nitrite concentration. For example, at 10 µg/ml concentration, the *S. indicus* extract (LI12500) and *C. aromaticus* extract (LI34103) exhibited 10.64% and −1.8% nitrite concentrations respectively. Whereas the composition 1 (LI12522F2), which contains 2:1 ratio of *S. indicus* extract (LI12500) and *C. aromaticus* extract (LI34103) exhibited 20.8% nitrite concentration. This nitrite concentration level in the cells treated with the compositions is higher than that in the cells treated with the individual components.

The Nitrate assay was conducted using composition-4 (LI12532F1) and individual extracts of *S. indicus* (LI12500), *C. aromaticus* (LI34103) and *G. mangostana* (LI80013). The composition-4 (LI12532F1) clearly shows the synergistic activity at both tested concentrations of 10 and 25 µg/ml. The results of this study showed that composition-4 (LI12532F1) exhibited greater enhancing nitrate concentration activity than the individual extracts. For example at 25 µg/ml concentration in the Table 2, *S. indicus* extract (LI12500), *C. aromaticus* extract (LI34103) and *G. mangostana* extract (LI80013) exhibited 5.08%, 21.55% and 109.32% nitrate concentration. Whereas the composition-4 (LI12532F1) exhibited 193.99% nitrate concentration at 25 µg/ml. The nitrate concentration enhancing activity with the composition-4 (LI12532F1) is higher than that the individual extracts.

TABLE 2

| S. No. | Test Product | Code | Nitrite Concentration (%) at 10 µg/ml | Nitrite Concentration (%) at 25 µg/ml |
|---|---|---|---|---|
| 1 | Composition-4 | LI12532F1 | 95.2 | 193.99 |
| 2 | *S. indicus* extract | LI12500 | 2.15 | 5.08 |
| 3 | *C. aromaticus* extract | LI34103 | 11.68 | 21.55 |
| 4 | *G. mangostana* extract | LI80013 | 53.13 | 109.32 |

TABLE 3

| S. No. | Test product | Code | Nitrite Concentration (%) at 1 µg/ml |
|---|---|---|---|
| 1 | Composition-7 | LI89034F1 | 79.10 |
| 2 | *C. quadrangularis* extract | LI05704 | −13.11 |
| 3 | *C. longa* extract | LI09703 | 36.25 |
| 4 | *T. ammi* extract | LI12304 | 20.52 |

The above nitrite concentration values (Table 3), clearly shows the synergistic efficacy of the composition-7 (LI89034F1) in enhancing nitrite concentration. For example, at 1 µg/ml concentration, *C. quadrangularis* (LI05704), *C. longa* (LI09703) and *T. ammi* (LI12304) exhibited −13.11%, 36.25% and 20.52% nitrite concentrations respectively. Whereas the composition-7 (LI89034F1), which contains 1:2:1 ratio of *C. quadrangularis* (LI05704), *C. longa* (LI09703) and *T. ammi* (LI12304) exhibited 79.10% nitrite concentration. This nitrite concentration level in the cells treated with the composition-7 (LI89034F1) is higher than that in the cells treated with the individual components. So the nitrate enhancing activity of composition-7 (LI89034F1) is higher than the individual extracts.

Example 6: ATP Assay

Cellular ATP content was measured in rat skeletal muscle cells using ATPlite assay kit (Perkin Elmer). Briefly, L6 rat skeletal muscle cells were grown in a 96 well plate in RPMI, supplemented with 10% FBS and 500 g/ml of penicillin-streptomycin at 37° C. with 5% CO2. After 16 h, media was replaced with fresh media containing independently *Spaeranthus indicus* extract (LI12500) and its compositions (LI12522F2 and LI12532F1); *Cissus quadrangularis* extract (LI05704), and its compositions (LI89032F3 and LI89034F1; *Garcinia mangostana* extract (LI80013) and its composition (LI80020F3) in combination with *Cinnamomum tamala* extract (LI33603); *Citrullus lanatus* extract (LI/PD/151/01R1) and *Ocimum sanctum* extract (LI/PD/014/03R1) and incubated for 4 hours. The vehicle control cultures received only 0.2% DMSO. Thereafter, 50 µl cell lysis buffer was added to each well and incubated for 5 min under controlled shaking condition. The evaluation of ATP concentrations of different cell lysates so obtained were conducted following the method provided by the vendor (Perkin Elmer Life Sciences, Boston, Mass.). The standard wells contain various concentrations of ATP ranging from 10 µM to 0.15 µM. Fifty micro liters of substrate solution was added to each well and allowed to mix on a shaker for 15 min under dark condition. Finally, the luminescence intensity was measured in a microplate reader Spectra MaxM5 (Molecular devices, Sunnyvale, Calif.). ATP content in the cell lysates obtained from the cells treated with individual extracts or compositions was measured by plotting the luminescence intensities into the standard curve constructed from the known ATP concentrations. The cellular ATP index in the treated cultures was calculated by comparing the ATP content in the treated samples with the ATP content in the vehicle control cultures. The ATP content in the vehicle control cultures was considered as 100 percent. All treatment concentrations for each sample were treated in quadruplicate wells.

TABLE 4

| S. No. | Test Product at the Dose of 10 pg/ml | Code | ATP Concentration (%) |
|---|---|---|---|
| 1. | S. indicus extract | LI12500 | 87.61 |
| 2. | C. aromaticus extract | LI34103 | 95.63 |
| 3. | Composition-1 | LI12522F2 | 137.24 |
| 4. | C. quadrangularis extract | LI05704 | 129.04 |
| 5. | C. longa extract | LI09703 | 85.21 |
| 6. | Composition-2 | LI89032F3 | 157.10 |
| 7. | G. mangostana extract | LI80013 | 94.39 |
| 8. | C. tamala extract | LI33603 | 84.66 |
| 9. | Composition-3 | LI80020F3 | 148.91 |

The ATPlite assay kit and the ATP concentration (%) data is summarized in Table 4. The data reveled that all the compositions showed an increase in the ATP content with a significant synergistic effect. The results of this study showed that composition of the extracts showed greater ATP concentration than the individual extracts. For example, at 10 pg/ml concentrations, the C. quadrangularis extract (LI05704) and C. longa extract (LI09703) exhibited 129.04% and 85.21% ATP concentration respectively. Whereas the composition 2 (LI89032F3), which contains 1:2 ratio of C. quadrangularis extract (LI05704) and C. longa extract (LI09703) exhibited 157.1% ATP concentration.

TABLE 5

| S. No. | Test Product | Code | ATP Concentration (%) at 10 pg/ml |
|---|---|---|---|
| 1 | Composition-4 | LI12532F1 | 153.01 |
| 2 | S. indicus extract | LI12500 | 86.93 |
| 3 | C. aromaticus extract | LI34103 | 95.65 |
| 4 | G. mangostana extract | LI80013 | 124.24 |

Cellular ATP content was measured in rat skeletal muscle cells using the extracts of S. indicus (LI12500), C. aromaticus (LI34103) and G. mangostana (LI80013). Table 5 shows the values of ATP content at 10 pg/ml concentration. The composition-4 (LI12532F1) containing S. indicus (LI12500), C. aromaticus (LI34103) and G. mangostana (LI80013) exhibited good synergistic activity with an increased ATP content of 153.01% at 10 pg/ml concentration. Whereas, the individual extracts showed lower activity than the composition with an ATP content of 86.93% for S. indicus (LI12500), 95.65% for C. aromaticus (LI34103) and 124.24% for G. mangostana (LI80013) at 10 pg/ml. This unexpected result clearly shows the synergistic activity of the composition-4 with an increased ATP concentration.

TABLE 6

| S. No. | Test product | Code | ATP Concentration (%) at 1000 pg/ml |
|---|---|---|---|
| 1 | Composition-7 | LI89034F1 | 158.57 |
| 2 | C. quadrangularis extract | LI05704 | 105.25 |
| 3 | C. longa extract | LI09703 | 119.46 |
| 4 | T. ammi extract | LI12304 | 144.94 |

The results from ATP assay (Table 6), clearly shows the synergistic efficacy of the composition-7 (LI89034F1) in enhancing ATP concentration. For example, at 1000 pg/ml concentration, C. quadrangularis (LI05704), C. longa (LI09703) and T. ammi (LI12304) exhibited 105.25%, 119.46% and 144.94% ATP concentrations respectively. Whereas the composition-7 (LI89034F1), which contains 1:2:1 ratio of C. quadrangularis (LI05704), C. longa (LI09703) and T. ammi (LI12304) exhibited 158.57% ATP concentration. This ATP levels in the cells treated with the composition-5 is higher than that in the cells treated with the individual components. So the ATP increasing activity of composition-7 (LI89034F1) is higher than the individual extracts.

Example 7—Protein Assay

Protein synthesis enhancing efficiency of Sphaeranthus indicus extract (LI12500) and its compositions (LI12522F2 and LI12532F1) in combination with Coleus aromaticus extract (LI34103) as well as with Garcinia mangostana extract (LI80013); Cissus quadrangularis extract (LI05704), and its compositions (LI89032F3 and LI89034F1) in combination with Curcuma longa extract (LI09703) as well as with Trachyspermum ammi extract (LI12304); Garcinia mangostana extract (LI80013) and its composition (LI80020F3) in combination with Cinnamomum tamala extract (LI33603); Citrullus lanatus extract (LI/PD/151/01R1) and Ocimum sanctum extract (LI/PD/014/03R1) was assessed in L6 rat skeletal muscle cells. Equal number of L6 cells was grown in each well of 96 well cell culture plates. Next day, the cells were treated with various concentrations of the Sphaeranthus indicus extract, Coleus aromaticus extract, Cissus quadrangularis extract, Garcinia mangostana extract, Curcuma longa extract and Cinnamomum tamala extract; and their compositions LI89032F3, LI89034F1, LI12522F2, LI12532F1 and LI80020F3 and the treatment phase was continued till 72 h. The vehicle control culture well received only 0.2% DMSO. After the treatment period, cells were washed twice with phosphate buffered saline (PBS). Thereafter, the cells were lysed in 1% SDS. The protein content in the cell lysates was measured using BCA Protein Assay kit (Thermo Scientific). Bovine serum albumin at different concentrations ranging from 25 µg/ml to 0.78 ug/ml was used as the standard. The absorbance of the color reaction was read at 562 nm in a microplate reader Spectra MaxM5 (Molecular devices, Sunnyvale, Calif.). The protein content in the cell lysates was quantitatively measured by plotting the absorbance values into the standard curve constructed from the known protein concentrations in standard wells.

TABLE 7

| S. No. | Test Product at the Dose of 1 ng/ml | Code | Protein Concentration (%) |
|---|---|---|---|
| 1. | S. indicus extract | LI12500 | 105.25 |
| 2. | C. aromaticus extract | LI34103 | 82.70 |
| 3. | Composition-1 | LI12522F2 | 128.49 |
| 4. | C. quadrangularis extract | LI05704 | 93.47 |
| 5. | C. longa extract | LI09703 | 106.12 |
| 6. | Composition-2 | LI89032F3 | 121.12 |
| 7. | G. mangostana extract | LI80013 | 104.23 |
| 8. | C. tamala extract | LI33603 | 90.14 |
| 9. | Composition-3 | LI80020F3 | 115.69 |
| 10. | C. lanatus extract | LI/PD/151/01R1 | 105.96 |
| 11. | O. sanctum extract | LI/PD/014/03R1 | 107.24 |

The dietary supplement compositions are screened for their protein synthesis efficiency in L6 rat skeletal muscle cells. All the tested compositions exhibited synergistic effect and more effective in increasing the content of protein in the skeletal muscle cell as summarized in Table 7. For example, at 1 ng/ml concentration, the G. mangostana extract (LI80013) and C. tamala extract (LI33603) exhibited 104.23% and 90.14% protein concentration respectively.

Whereas the composition 3 (LI80020F3), which contains 1:2 ratio of G. mangostana extract (LI80013) and C. tamala extract (LI33603) exhibited 115.69% protein concentration.

Animal Study
Energy and Endurance FST Study Procedure

Swiss albino mice were acclimatized for 5 days before initiation of the study. Healthy Swiss albino mice were selected and randomly divided (n=6) into different treatment groups. The animals were orally treated with vehicle or 150 mg/kg of LI89032F3 or LI12522F2 or LI80020F3 or 150 mg/kg of L-Carnitine or 10 mg/kg Caffeine for 21 days.

On day 21, one hour after the treatment the mice were forced to swim with a constant load (10% of its body weight attached to its tail) in an acrylic cylinder filled with water. This test was monitored for 10 minutes using the SMART video tracking system (Panlab S.L.U). Various swimming parameters were recorded and analyzed by smart software. Measured Swimming parameters include, resting time, slow moving time, fast moving time, total moving time, path length of swimming and average velocity. The results were expressed as mean±SEM and compared with control group to measure efficacy and were summarized in Table 8.

Swiss albino mice were administered with LI12522F2, LI89032F3, LI80020F3, Caffeine and L-Carnitine orally at the dose of 150 mg/kg of LI89032F3 or LI12522F2 or LI80020F3 or L-Carnitine or 10 mg/kg of Caffeine respectively, to evaluate the energy endurance and muscle strength potential of these compounds. The animal groups supplemented with the test items LI12522F2, LI89032F3, LI80020F3, L-Carnitine and standard drug caffeine showed a reduction in resting time (sec) and increase in distance traveled (mm), slow swimming time (sec), fast swimming time (sec) on day 21 of the study. The above observations indicate that the animals treated with LI12522F2, LI89032F3, LI80020F3, Caffeine and L-Carnitine were more active and energetic during 10 minutes of forced swimming period and could tend to swim either slow or fast most of the time rather than resting as compared to control group. The increase in percent fast swimming and swimming velocity in group on day 21 reveals that the treated animals tends to swim fast and covered longer distances in the shortest period of time after oral administration of LI12522F2, LI80020F3, LI89032F3 as compared to control group. Hence, the animals treated with these compositions LI12522F2, LI80020F3, LI8903 are more energetic. In addition, an improved energy the increase in distance traveled and reduced resting time indicate that the compositions LI12522F2, LI80020F3, LI89032F3 have higher endurance over the control.

TABLE 8

| Parameters | FST Control (n = 4) | LI12522F2 (n = 6) | LI89032F3 (n = 6) | LI80020F3 (n = 6) | Caffeine (n = 6) | L-Carnitine (n = 6) |
|---|---|---|---|---|---|---|
| Distance Travelled (mm) | 20796.52 ± 1074.47 | 26978.04 ± 1017.94 | 26956.58 ± 2880.10 | 25642.08 ± 2247.29 | 28740.25 ± 3297.91 | 26197.58 ± 3117.55 |
| Resting Time (sec) | 474.10 ± 9.44 | 431.48 ± 11.94 | 416.97 ± 26.44 | 446.44 ± 20.84 | 399.64 ± 27.89 | 419.52 ± 27.83 |
| Slow Swimming | 78.60 ± 6.90 | 102.24 ± 7.67 | 102.40 ± 16.03 | 94.00 ± 15.64 | 92.12 ± 10.74 | 104.92 ± 18.89 |
| Fast Swimming Time (sec) | 48.55 ± 3.16 | 71.68 ± 6.20 | 74.23 ± 11.07 | 61.72 ± 6.26 | 82.16 ± 15.05 | 67.64 ± 10.72 |
| Average Velocity | 34.59 ± 1.79 | 44.56 ± 1.70 | 45.45 ± 4.90 | 42.61 ± 3.75 | 49.80 ± 4.48 | 44.24 ± 5.25 |

Values are expressed as Mean ± SEM; n = 6 animals/group

Grip Strength Measurement

Swiss albino mice were acclimatized for 5 days before initiation of the study. Healthy Swiss albino mice were selected and randomly divided (n=6) into different treatment groups. The animals were orally treated with vehicle or 150 mg/kg of LI89032F3 or LI12522F2 or LI80020F3 or 150 mg/kg of L-Carnitine or 10 mg/kg Caffeine for 21 days.

After 21 days of treatment Grip strength of mice was measured by using Grip strength meter (UgoBasile, Italy). Animals were trained and habituated to the experimental environment and conditions for 5 days. Each mice was allowed to grasp the grasping bar and it was pulled back gently in a horizontal plane by tail with gradually increasing force till the pulling force overcomes the grip strength of the animal. The force applied at the moment when the mice leaves its grasp on the grasping bar was recorded as grip strength in grams. Three trials were conducted on each animal and average grip strength was calculated. The results were expressed as mean±SEM and compared with control group and were summarized in Table 9.

TABLE 9

| Group | Average Grip Strength measured after 21 Days |
|---|---|
| FST control | 57.00 ± 4.04 |
| LI12522F2 | 73.73 ± 5.22 |
| LI89032F3 | 70.33 ± 3.50 |
| LI80020F3 | 68.80 ± 6.42 |
| Caffeine | 56.07 ± 10.37 |
| L-Carnitine | 39.20 ± 7.51 |

Values are expressed as Mean ± SEM; n = 6 animals/group

Based on the data, it is obvious that animal group treated with compositions LI12522F2, LI80020F3 and LI89032F2 for 21 days exhibited relatively better grip strength when compared control.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A composition comprising a synergistic mixture of from 20% to 80% of an extract of *Cinnamomum tamala* and from 20% to 80% of an extract of *Garcinia mangostana*, based on the weight of the composition.

2. The composition according to claim 1, which further comprises at least one extract selected from the group consisting of extracts of *Sphaeranthus indicus, Curcuma longa, Cissus quadrangularis, Coleus aromaticus, Citrullus lanatus, Ocimum sanctum*.

3. The composition according to claim 1, which further comprises at least one biologically active extract selected from the group consisting of extracts of *Ocimum basilicum, Zingiber officinalis, Tribulus terrestris, Trachyspermum ammi, Mentha arvensis, Piper cubeba* and *Foeniculum vulgare*.

4. The composition according to claim 2, which further comprises at least one biologically active extract selected from the group consisting of extracts of *Ocimum basilicum, Zingiber officinalis, Tribulus terrestris, Trachyspermum ammi, Mentha arvensis, Piper cubeba* and *Foeniculum vulgare*.

5. A composition according to claim 1, comprising a synergistic mixture of the extract of *Cinnamomum tamala* and the extract of *Garcinia mangostana* in a 2:1 ratio, based on the weight of the composition.

6. The composition according to claim 1, further comprising at least one ingredient selected from the group consisting of excipients, diluents, sweeteners, flavorants colorants, vitamins and amino acids.

7. The composition according to claim 2, further comprising at least one ingredient selected from the group consisting of excipients, diluents, sweeteners, flavorants, colorants, vitamins and amino acids.

8. A solid oral dosage form selected from the group consisting of a tablet, a capsule, and a chewable dosage form, comprising the composition of claim 1.

9. A tablet, comprising the composition of claim 1.

10. A tablet according to claim 9, wherein the tablet is a controlled release tablet.

11. A method of enhancing natural energy, improving muscle strength, muscle mass and/or mental alertness in a warm blooded animal or mammal in need thereof, wherein the method comprises administering to a subject or mammal or warm blooded animal a therapeutically effective quantity of a composition according to claim 1.

12. The method according to claim 11, wherein the composition further comprises at least one extract selected from the group consisting of extracts of *Sphaeranthus indicus, Curcuma longa, Cissus quadrangularis, Coleus aromaticus, Citrullus lanatus*, and *Ocimum sanctum*.

13. The method according to claim 11, wherein the composition further comprises at least one biologically active extract selected from the group consisting of extracts of *Ocimum basilicum, Zingiber officinalis, Tribulus terrestris, Trachyspermum ammi, Mentha arvensis, Piper cubeba* and *Foeniculum vulgare*.

14. The method according to claim 12, wherein the composition further comprises at least one biologically active extract selected from the group consisting of extracts of *Ocimum basilicum, Zingiber officinalis, Tribulus terrestris, Trachyspermum ammi, Mentha arvensis, Piper cubeba* and *Foeniculum vulgare*.

15. The method according to claim 11, wherein the composition comprises a mixture of the extract of *Cinnamomum tamala* and the extract of *Garcinia mangostana* in a 2:1 ratio.

16. The method according to claim 11, wherein the composition further comprises at least one ingredient selected from the group consisting of excipients, diluents, sweeteners, flavorants colorants, vitamins and amino acids.

17. A method for at least one of:
   a) affecting the concentration of at least one compound selected from the group consisting of ATP, Nitric Oxide, Muscle protein, Miogenin; and
   b) enhancing muscle cell proliferation;
   wherein the method comprises administering to a subject or mammal or warm blooded animal a therapeutically effective quantity of a composition comprising:
   a synergistic mixture of from 20% to 80% of an extract of *Cinnamomum tamala* and from 20% to 80% of an extract of *Garcinia mangostana*.

18. The method according to claim 17, wherein the composition further comprises an extract selected from the group consisting of extracts of *Sphaeranthus indicus, Curcuma longa, Cissus quadrangularis, Coleus aromaticus, Citrullus lanatus, Ocimum sanctum*.

19. The method according to claim 17, wherein the composition comprises a mixture of the extract of *Cinnamomum tamala* and the extract of *Garcinia mangostana* in a 2:1 ratio.

* * * * *